(12) United States Patent
Zemla

(10) Patent No.: US 8,024,127 B2
(45) Date of Patent: Sep. 20, 2011

(54) LOCAL-GLOBAL ALIGNMENT FOR FINDING 3D SIMILARITIES IN PROTEIN STRUCTURES

(75) Inventor: Adam T. Zemla, Brentwood, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 773 days.

(21) Appl. No.: 10/782,061

(22) Filed: Feb. 18, 2004

(65) Prior Publication Data

US 2004/0185486 A1 Sep. 23, 2004

Related U.S. Application Data

(60) Provisional application No. 60/451,292, filed on Feb. 27, 2003.

(51) Int. Cl.
*G01N 33/48* (2006.01)
(52) U.S. Cl. .......................................... 702/19; 703/11
(58) Field of Classification Search .................. 702/19, 702/27
See application file for complete search history.

(56) References Cited

U.S. PATENT DOCUMENTS

| 2002/0150906 A1 | 10/2002 | Debe |
| 2003/0130797 A1 | 7/2003 | Skolnick et al. |

FOREIGN PATENT DOCUMENTS

| WO | WO 93/01484 | 1/1993 |
| WO | WO 98/48270 | 10/1998 |
| WO | WO 00/11206 | 3/2000 |

OTHER PUBLICATIONS

Zemla et al. Proteins: Structure, Function, and Genetics vol. 45, Issue S5, pp. 13-21. Published Online: Jan. 28, 2002.*
Cristobal et al. BMC Bioinformatics 2001, 2:5. Published Aug. 1, 2001.*
Zemla et al. Processing and analysis of casp3 protein structure predictions. Proteins: Struct. Funct. Genet. 1999, Suppl 3:22-29.*
Zemla, A., "LGA: a method for finding 3D similarities in protein structures," Nucleic Acids Research, Oxford University Press, vol. 31, No. 13, 2003, pp. 3370-3374.
Zu-Kang, F., et al., "Optimum superimposition of protein structures: ambiguities and implications," Research Paper, Folding & Design, Center for Applied Molecular Engineering, Institute for Chemistry and Biochemistry, University of Salzburg, Austria, Feb. 26, 1996, pp. 123-132.
Lackner, P., et al., "ProSup: a refined tool for protein structure alignment," Protein Engineering, Oxford University Press, vol. 13, No. 11, 2000, pp. 745-752.
Shindyalov, I., et al., "Protein structure alignment by incremental combinatorial extension (CE) of the optimal path," Protein Engineering, vol. 11, No. 9, 1998, pp. 739-747.
Holm, L., et al., "Protein Structure Comparison by Alignment of Distance Matrices," J. Mol. Biol., vol. 233, 1993, pp. 123-138.
Kopp, J., et al., "The Swiss-Model Repository of annotated three-dimensional protein structure homology models," Nucleic Acids Research, Database issue, 2004, pp. D230-D234, vol. 32.
Lengauer, T., et al., "Protein structure prediction methods for drug design," Briefings in Bioinformatics, Sep. 2000, pp. 275-288, vol. 1, No. 3, Henry Steward Publications.
Slezak, T., et al., "Comparative genomics tools applied to bioterrorism defense," Briefings in Bioinformatics, Jun. 2003, pp. 133-149, vol. 4, No. 2.
Takeda-Shitaka, M., et al., "Protein Structure Prediction in Structure based Drug Design", Current Medicinal Chemistry, 2004, pp. 551-558, vol. 11, No. 5.

* cited by examiner

*Primary Examiner* — Michael Borin

(57) ABSTRACT

A method of finding 3D similarities in protein structures of a first molecule and a second molecule. The method comprises providing preselected information regarding the first molecule and the second molecule. Comparing the first molecule and the second molecule using Longest Continuous Segments (LCS) analysis. Comparing the first molecule and the second molecule using Global Distance Test (GDT) analysis. Comparing the first molecule and the second molecule using Local Global Alignment Scoring function (LGA_S) analysis. Verifying constructed alignment and repeating the steps to find the regions of 3D similarities in protein structures.

8 Claims, 3 Drawing Sheets

LOCAL-GLOBAL ALIGNMENT FOR FINDING 3D SIMILARITIES IN PROTEIN STRUCTURES

CROSS-REFERENCE TO RELATED APPLICATIONS

This application claims the benefit of U.S. Provisional Patent Application No. 60/451,292 filed Feb. 27, 2003 and titled "Local-Global Alignment—a Method for Finding 3D Similarities in Protein Structures." U.S. Provisional Patent Application No. 60/451,292 filed Feb. 27, 2003 and titled "Local-Global Alignment—a Method for Finding 3D Similarities in Protein Structures" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to obtaining information about protein and more particularly to finding 3D similarities in protein structures.

2. State of Technology

U.S. patent application Ser. No. 2002/0150906 by Derek A. Debe, published Oct. 17, 2002, for a method for determining three-dimensional protein structure from primary protein sequence provides the following state of technology information:

"While the sequencing of the human genome is a landmark achievement in genomics, it also creates the next great challenge, namely to create an accurate structural model of each protein coded by the human genome. Since the experimental determination of all of the protein structures coded would require decades, computational methods for determining three-dimensional protein structures are essential if structural genomics is going to rapidly progress. . . .

Proteins are linear polymers of amino acids. Naturally occurring proteins may contain as many as 20 different types of amino acid residues, each of which contains a distinctive side chain. The particular linear sequence of amino acid residues in a protein defines the primary sequence, or primary structure, of the protein. The primary structure of a protein can be determined with relative ease using known methods. . . .

Proteins fold into a three-dimensional structure. The folding is determined by the sequence of amino acids and by the protein's environment. Examination of the three-dimensional structure of numerous natural proteins has revealed a number of recurring patterns. Patterns known as alpha helices, parallel beta sheets, and anti-parallel beta sheets are commonly observed. . . .

The biological properties of a protein depend directly on its three-dimensional (3D) conformation. The 3D conformation determines the activity of enzymes, the capacity and specificity of binding proteins, and the structural attributes of receptor molecules. Because the three-dimensional structure of a protein molecule is so significant, it has long been recognized that a means for easily determining a protein's three-dimensional structure from its known amino acid sequence would be highly desirable. However, it has proven extremely difficult to make such a determination without experimental data. . . .

In the past, the three-dimensional structures of proteins have been determined using a number of different experimental methods. Perhaps the recognized methods of determining protein structure involves the use of the technique of x-ray crystallography. . . .

These experimental techniques all suffer from at least one significant shortcoming. Namely, they are labor intensive and therefore slow and expensive. Modern sequencing techniques are creating rapidly growing databases of primary sequences that need to be translated into three dimensional protein structures. Indeed, with more than 500 genomes including the human genome fully sequenced, three dimensional structures have only been determined for about 2% of these sequences. Every day the ratio of predicted-three dimensional structures to primary sequences is getting smaller. . . .

In order to more rapidly predict three dimensional structures from primary sequences, biochemists are turning to various computational approaches that permit structure determination to be done with computers and software rather than laborious and intricate laboratory techniques. One of the most promising of these computational approaches compares the similarity of a primary sequence for which the three dimensional structure of the sequence is sought, referred to throughout as a query sequence or a query peptide against one or more primary sequences, usually a database of such sequences, referred to throughout as template sequences or template peptides, for which the three dimensional structures are known. This is one aspect of primary sequence homology modeling. . . .

At a high level, many primary sequence homology modeling methods can be characterized in two steps. In the first step, referred to as the alignment step, the query sequence for which the three dimensional structure is sought, is aligned against one or more template sequences, contained in a database. The three dimensional structures for each of the template sequences are known in whole or in substantial part. After each alignment comparison between the query peptide and a template peptide, the method gives a score. After each comparison has been made in the database, the highest scoring alignment pair reflects the optimally aligned query sequence/template sequence(s). The optimal sequence alignment may be used to generate the most accurate structural determinations regarding the query sequence. Still, a query/template alignment producing a sub-optimal score may be used to generate useful structural information regarding the query sequence. . . .

In the second step, referred to as the modeling step, structural information of the query peptide may be predicted based upon structural information corresponding to the sequence or subsequences aligned in the template sequence. The most common of primary sequence homology methods use sequence homologies to predict the three dimensional structure of a query sequence based on the three dimensional structure of aligned template sequences. Still, other primary sequence homology modeling techniques seek to determine primary sequence homology relationships between one or more query sequences based on the primary sequences of aligned template sequences."

U.S. patent application Ser. No. 2003/0130797 by Jeffery Skolnick and Andrzej Kolinski, published Jul. 10, 2003, for protein modeling tools provides the following state of technology information:

"To maximize the utility of such nucleotide sequence information, it must be interpreted. Various tools have been developed to assist in this process. For example, algorithms have been developed to analyze what a particular nucleotidesequence encodes, e.g., a regulatory region, an open reading frame (ORF), particularly for protein sequences, or a non-translated RNA, based on homology with known sequences (which are presumed to have similar structures and related functions). See, e.g., "Frames" (Genetics Computer Group, Madison, Wis.; www.gcg.com), which is used for identifying ORFs. For sequences predicted or determined to be ORFs, it is possible to determine the amino acid sequence of the protein encoded thereby using simple analytical tools well known in the art. For example, see "Translate" (Genetics Computer Group, Madison, Wis.; www.gcg.com). However, to date determination of the primary structure of a protein in and of itself provides little, if any, functional information about the protein or its corresponding gene. Thus, the ability to predict the three-dimensional structure of a protein from its amino acid sequence is of great theoretical and practical importance."

International Patent Application No. WO 98/48270 by William Goddard et al., for a method of determining three-dimensional protein structure from primary protein sequence, published Oct. 29, 1998 provides the following state of technology information:

"Since the seminal work by C. B. Anfinsen, determining the three-dimensional structure of a protein from its amino acid sequence has been a much sought after goal in structural and computational biology. However, although progress has been made in several fronts such as secondary structure I prediction and homology modeling, a general method for ab initio structure prediction, or in other words, a solution to the so-called "protein folding problem, "has eluded investigators."

International Patent Application No. WO 93/01484 by David Eisenberg et al., for a method to identify protein sequences that fold into a known three-dimensional structure, published Jan. 21, 1993, provides the following state of technology information:

"A computer-assisted method for identifying protein sequences that fold into a known three-dimensional structure. The inventive method attacks the inverse protein folding problem by finding target sequences that are most compatible with profiles representing the structural environments of the residues in known three-dimensional protein structures. The method starts with a known three-dimensional protein structure and determines three key features of each residue's environment within the structure: (1) the total area of the residue's side-chain that is buried by other protein atoms, inaccessible to solvent; (2) the fraction of the side-chain area that is covered by polar atoms (O, N) or water, and (3) the local secondary structure. Based on these parameters, each residue position is categorized into an environment class. In this manner, a three-dimensional protein structure is converted into a one-dimensional environment string, which represents the environment class of each residue in the folded protein structure. A 3D structure profile table is then created containing score values that represent the frequency of finding any of the 20 common amino acids structures at each position of the environment string. These frequencies are determined from a database of known protein structures and aligned sequences. The method determines the most favorable alignment of a target protein sequence to the residue positions defined by the environment string, and determines a "best fit" alignment score, Sij for the target sequence. Each target sequence may then be further characterized by a ZScore, which is the number of standard deviations that Sij for the target sequence is above the mean alignment score for other target sequences of similar length." International Patent Application No. WO 93/01484 is incorporated into this application by reference.

International Patent Application No. WO 00/11206 by Jeffrey Skolnick et al., for methods and systems for predicting protein function, published Mar. 2, 2000 provides the following state of technology information:

" . . . methods and systems for predicting the biological function(s) of proteins . . . based on the development of functional site descriptors for discrete protein biological functions. Functional site descriptors are geometric representations of protein functional sites in three-dimensional space, and can also include additional parameters, for example, conformational information. Following their development, one or more functional site descriptors (for one or more different biological functions) are used to probe protein structures to determine if such structures contain the functional sites described by the corresponding functional site descriptors. If so, the protein(s) containing the functional site(s) are predicted to have the corresponding biological function(s) . . . a library of functional site descriptors is used to probe inexact protein structures derived by computational methods from amino acid sequence information to predict the biological function(s) of such sequences and of the gene(s) encoding the same." International Patent Application No. WO 00/11206 is incorporated into this application by reference.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a Local-Global Alignment (LGA) that finds similarities between two structures and fragments of protein structures. It allows identification and analysis of structural similarities of proteins that do not have significant amino acid sequence similarity. It allows clustering of similar fragments of structures. Such clusters can be used to identify sequence patterns which will represent local structural motifs in proteins. The use of LGA improves the process of fold recognition and more distant homologs detection, and also in protein structure prediction methods will enhance the quality and accuracy of the final 3D protein models produced especially when small fragments of proteins need to be modeled (loops, deletions, insertions, signature regions).

The present invention has many uses. The uses include, but are not limited to: structural comparison of proteins, structural superposition of proteins, finding similarities between protein structures or fragments of protein structure, clustering similar fragments of protein structures, creating database of similar fragments of protein structures with corresponding amino acids sequence patterns, analysis of protein structure, homology modeling, and modeling of small fragments of proteins (loops, insertions, deletions, signature regions).

One embodiment of the present invention provides a method of finding 3D similarities in protein the structure of a first molecule and of a second molecule. The method comprises processing preselected structure information of alignment of residue-residue correspondence, comparing the first molecule and the second molecule using the preselected information and using Longest Continuous Segments (LCS) analysis, comparing the first molecule and the second molecule using the preselected information and using Global Distance Test (GDT) analysis, comparing the first molecule and the second molecule using the preselected information and using Local Global Alignment Scoring function (LGA_S) analysis, repeating the steps to find all the regions of 3D similarities between considered protein structures, and generating an output containing complete information about the quality of the calculated alignment.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 2 is FIG. 1A in the journal article LGA: a method for finding 3D similarities in protein structures by Adam Zemla, in the journal, Nucleic Acids Research, 2003, Vol. 31, No. 13, pp. 3370-3374.

FIG. 3 is FIG. 1B in the journal article LGA: a method for finding 3D similarities in protein structures by Adam Zemla, in the journal, Nucleic Acids Research, 2003, Vol. 31, No. 13, pp. 3370-3374.

FIG. 6 is FIG. 2A in the journal article LGA: a method for finding 3D similarities in protein structures by Adam Zemla, in the journal, Nucleic Acids Research, 2003, Vol. 31, No. 13, pp. 3370-3374.

DETAILED DESCRIPTION OF THE INVENTION

Figure 1:
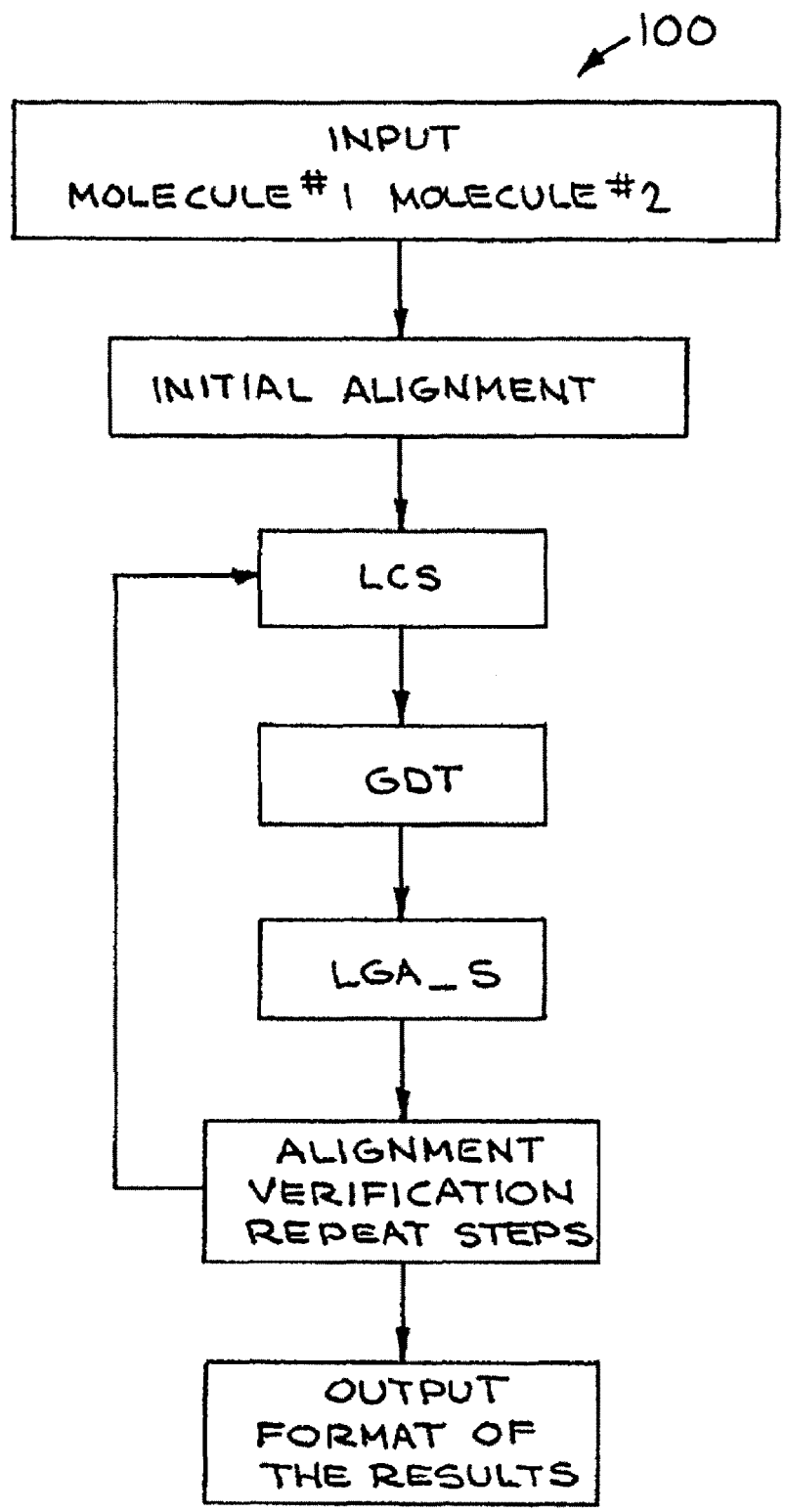
FIG. 1 is a flow chart illustrating an embodiment of the present invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

For given two protein structures the present invention provides a method of finding regions of 3D similarities in protein structures between a first molecule and a second molecule. The method comprises a number of following steps. Comparing the first molecule and the second molecule using Longest Continuous Segments (LCS) analysis. Comparing the first molecule and the second molecule using Global Distance Test (GDT) analysis. Evaluating the calculated alignment between the first molecule and the second molecule using Local Global Alignment Scoring function (LGA_S). For many different alignments repeating the steps above to find the complete set of local and global regions of 3D similarities between given two protein structures. The Local Global Alignment Scoring function (LGA_S) is described in greater detail in the following portions of the DETAILED DESCRIPTION OF THE INVENTION. The journal article LGA: a method for finding 3D similarities in protein structures by Adam Zemla, in the journal, Nucleic Acids Research, 2003, Vol. 31, No. 13, pp. 3370-3374 includes a section under the heading "Description of the LGA scoring function" which provides additional information about using Local Global Alignment Scoring function (LGA_S). The journal article LGA: a method for finding 3D similarities in protein structures by Adam Zemla, in the journal, Nucleic Acids Research, 2003, Vol. 31, No. 13, pp. 3370-3374 is incorporated herein in its entirety by this reference.

All these steps are illustrated on the FIG. 1 and described below:

1) an input to the LGA program consists of any two protein structures (Molecule-1 and Molecule-2) provided in standard PDB format
2) an initial alignment (residue-residue correspondence) between two molecules is automatically generated
3) for the given alignment LCS procedure is performed searching for the longest continuous segments of residue pairs that can be fit under the selected RMSD cutoffs (see LCS description below)
4) for the given alignment GDT procedure is performed searching for the largest (not necessarily continuous) segments of residue pairs that can be fit under the selected DISTANCE cutoffs (see GDT description below)
5) the results from LCS and GDT analyses are used to calculate scoring (fitness) function LGA_S (see LGA_S description below)
6) based on LGA_S score and generated structure superposition the alignment is evaluated and eventually modified (steps 3-6 will be repeated) or considered as final (residue-residue correspondence is reported using uniquely designed format of calculated results)
7) the output from the program provides the complete information about the quality of the calculated alignment (distances between the corresponding residues, LCS data and GDT data). The designed format of the output data allows to provide the comprehensive information about the regions of local and global similarities (see Table 1) between analyzed protein structures (Molecule-1 and Molecule-2)

In one embodiment, the Global Distance Test (GDT) analysis comprises the following steps: (a) for a given alignment apply the transform, (b) identify all atom pairs for which the distance is larger than the threshold, (c) re-obtain the transform, excluding those atoms, (d) modify an alignment and repeat steps (b)-(d) to find the largest set of residue pairs that can fit under the selected distance cutoff.

Referring now to FIGS. 1, 2, 3, 4, and 5, a system is illustrated that takes into account both local and global structure superpositions and also is capable of working without a preassigned residue correspondence. The system is designated generally by the reference numeral 100. The system 100 is called "LGA" for local/global alignment. The system 100 utilizes algorithms and applies the LGA program to test examples in order to highlight some of its features. Some of the structure comparison programs are built on the principle that a suitable scoring function can be defined with its optimum corresponding to the most significant structural match. Comparison techniques evaluate structural similarity by two numbers, the RMSD between two superimposed structures together with the number of "equivalent" (structurally aligned) residues. It is very difficult to optimize these two quantities simultaneously, since one can be optimized on the expense of the other. For example, the structural aligner DALI [DALI], which is based on the alignment of distance matrices, solves the optimization problem by combining several numbers to a single quantity, called z-score, ProSup aligner [ProSup-1, ProSup-2] maximizes the number of equivalent residues while RMSD is kept close to the constant value. An additional problem can arise if analyzed structures are similar only in small local regions and these regions of similarity cannot be recognized when one global superposition is applied. In general, in many cases there is no one "the best" superposition that can give us the whole picture of all regions of similarity between compared proteins.

To resolve these problems while comparing two structures, the LGA program generates many different local superpositions to detect regions where proteins are similar. As it was concluded in [ProSup-2] optimizing the number of equivalent residues while keeping the RMSD constant provides a simple and intuitive measure of structure similarity, and also can be used effectively for ranking in database searches. In LGA program an additional requirement of fulfilling DISTANCE restrictions together with a combination of the results from the extensive analysis of regions of local similarities was successfully implemented showing better performance in comparison with other programs like DALI, CE, and ProSup. The system is able to generate data that provide very detailed information about not only the level of global similarity but also about the regions of local similarity in protein structures. It allows clustering similar fragments of structures, and use such clusters to identify sequence patterns that would represent local structural motifs.

Genome sequencing projects require many new proteins to be characterized in terms of their structure and biochemical function. Although the cost and time to experimentally characterize such proteins is prohibitive, computational methods, based on amino acid sequence similarities (homology) between proteins, hold great promise in uncovering the structure and function of new proteins.

Referring now to FIG. 1, a flow chart illustrates system 100. As shown by FIG. 1, system 100 provides a method of finding 3D similarities in protein structures of a first molecule and a second molecule. The method comprises the steps of providing preselected information regarding the first molecule, providing preselected information regarding the second molecule, comparing the first molecule and the second molecule using Longest Continuous Segments (LCS) analysis, comparing the first molecule and the second molecule using Global Distance Test (GDT) analysis, comparing the first molecule and the second molecule using Local Global Alignment Scoring function (LGA_S) analysis, and repeating the steps to find the 3D similarities in protein structures.

The system 100 allows identification and analysis of structural similarities of proteins that do not have significant amino acid sequence similarity. The system 100 also allows clustering of similar fragments of structures. Such clusters can be used to identify sequence patterns which will represent local structural motifs in proteins. The system 100 generates data that can be used to analyze the correspondence between structure alignment (structure similarity) and sequence alignment (sequence similarity). The system 100 allows the selection and ranking of the regions of structure similarities in sequence.

In one embodiment, the Global Distance Test (GDT) analysis comprises the following steps, (a) obtain the transform, (b) apply the transform, (c) identify all atom pairs for which the distance is larger than the threshold, (d) re-obtain the transform.

The system 100 provides a Local-Global Alignment (LGA) that finds similarities between two structures (Molecule #1) and (Molecule #2) and fragments of protein structures. It allows identification and analysis of structural similarities of proteins that do not have significant amino acid sequence similarity. It allows clustering of similar fragments of structures. Such clusters can be used to identify sequence patterns which will represent local structural motifs in proteins. The use of LGA will significantly improve the process of fold recognition and more distant homologs detection, and also in protein structure prediction methods will enhance the quality and accuracy of the final 3D protein models produced especially when small fragments of proteins need to be modeled (loops, deletions, insertions, signature regions).

The system 100 has many uses. The uses include, but are not limited to, the following specific uses: structural comparison of proteins, structural superposition of proteins, finding similarities between protein structures or fragments of protein structure, clustering similar fragments of protein structures, creating database of similar fragments of protein structures with corresponding amino acids sequence patterns, analysis of protein structure, homology modeling, and modeling of small fragments of proteins (loops, insertions, deletions, signature regions).

In the last century, even before the shape of any proteins had been determined in atomic detail, it was understood that the macromolecular structure must be related to function. As soon as the first (determined at high resolution) enzyme structure, that of chymotrypsin, was discovered in 1967, a major question arose: How different are the structures of other proteins? According to a manually updated catalog of known protein structures, the SCOP database (Structural Classification of Proteins. 1.61 release), there are currently some 700 known folds, represented by about 17,500 experimentally determined protein structures deposited in PDB (Protein Data Bank).

The triumph of structural biology is that it allows a comparison of protein structures and thereby an understanding of their function. Catalytic active sites can be understood, conformational range can be explored, the potential exchange of ligands and substrates can be explored, the repertoire of nature can be measured, and so forth. Furthermore, major progress has been made in what can be described as the most important problem in structural biology, the protein folding problem, almost exclusively by capturing what is already known about how proteins fold. Moreover, when specific predictions are made, they can be assessed mostly by structural comparisons.

Comparison of two slightly different conformations of the same protein, the overall root mean square deviation (RMSD) of all corresponding C-alpha atoms gives a useful impression of the similarity between the two structures. Unfortunately, a small perturbation in just one part of the protein (e.g., in a hinge joining two domains) can create a large RMSD value and it would seem that the two structures are very different overall. Thus, it is desirable to consider also local regions of the proteins in assessing their similarity. In essence, the smaller such "deviant" regions, the more similar are the two structures. If one compares two different proteins, where there is not a preassigned correspondence between amino acid residues, a sequence-independent alignment (residue correspondence) has to be generated first, adding another significant level of complexity.

LGA program is developed for structure comparative analysis of two selected 3D protein structures or fragments of 3D protein structures. LGA generates data that can be used to analyze the correspondence between structure alignment (structure similarity) and sequence alignment (sequence similarity). This feature can significantly improve the process of homology modeling, fold recognition and enhance the quality and accuracy of the final 3D protein models produced (especially when small fragments of proteins need to be modeled). Structure comparative analysis can be made in two general modes: (1) Sequence dependent analysis. This mode can be used when two protein structures identical by the numbering of amino acid and the same chain id are to be investigated. Under this mode the program is able to identify the fragments where two structures are identical, and the fragments where they differ. And (2) Sequence independent analysis. This mode can be used for structural comparison of any two proteins. The best superposition (according to the LGA technique) is calculated completely ignoring sequence relationship between the two proteins, and the suitable amino acid correspondence (structural alignment) is reported.

In an attempt to generate detailed information about regions of local similarities between two protein structures or two segments of protein structures, the LGA program is capable to identify all largest sets of residues that can fit under a specified RMSD cutoff or DISTANCE cutoff. The procedure for searching an optimal superposition between two structures is the following. Each selected segment (set of residues) from each structure is used as a starting point to give an initial list of equivalent residues (selected atoms from Molecule1 and Molecule2) to generate a superposition. The list of equivalencies is iteratively extended to collect the largest set of residues that can fit under considered distance cutoff. The goal of the implemented iterative procedure is to exclude from the calculations atoms that are more distant than some threshold (distance cutoff) between the Molecule1 and the Molecule2 after the transform is applied.

Starting from the initial set of atoms pairs the algorithm is the following: (a) obtain the transform, (b) apply the transform, (c) identify all atom pairs for which distance is larger than the threshold, (d) re-obtain the transform, excluding those atoms, and (e) repeat b)-d) until the set of atoms used in calculations is the same for two cycles running.

Using this approach LGA program is capable to identify all largest sets of residues that can fit under a specified distance cutoff. To each residue the program assigns a number of such largest sets provided that the residue is a part of these sets. The system screens two structures every 0.5 A up to 10 A and reports possible superpositions.

The combination of these two (RMSD based and DISTANCE based) techniques of analyzing the similarities between protein structures allows the calculation of not only the final "best" (means: "under certain RMSD or DISTANCE cutoff") superposition, but also to identify and rank the regions of local similarities between compared structures. For example, in the structure alignment search procedure, for each generated list of equivalent residues the following values are calculated:

LCS_v—percent of residues (longest continuous segment) that can fit under RMSD cutoff of v Angstroms (v=1.0, 2.0, ...)

GDT_v—an estimation of the percent of residues (largest set, not necessary continuous) that can fit under the DISTANCE cutoff of v Angstroms (v=0.5, 1.0, 1.5, ...) and the combination of these values is used as a scoring function LGA_S to evaluate the level of structure similarity of selected regions. For a given parameter w (0.0<=w<=1.0) LGA_S can be defined as follows:

$$X = 0.0;$$
$$\text{for each vi (v1, v2, ..., vk)} \{$$
$$\quad Y = (k-i+1)/k; X = X + Y*F\_vi;$$
$$\}$$
$$S(F) = X/((1+k)*k/2);$$
and
$$LGA\_S = w*S(GDT) + (1-w)*S(LCS);$$

This approach is applied in LGA program to perform the selection and ranking of the regions of structure similarities in sequence dependent mode of analysis as well as in sequence independent mode. The LGA program is written in C language using standard library.

Genome sequencing projects require many new proteins to be characterized in terms of their structure and biochemical function. Although the cost and time to experimentally characterize such proteins is prohibitive, computational methods, based on amino acid sequence similarities (homology) between proteins, hold great promise in uncovering the structure and function of new proteins.

In a comparison of two slightly different conformations of the same protein, the overall root mean square deviation (RMSD) of all corresponding C-alpha atoms gives a useful impression of the similarity between the two structures. Unfortunately, a small perturbation in just one part of the protein (e.g., in a hinge joining two domains) can create a large RMSD, and it would seem that the two structures are very different overall. Thus, it is desirable to also consider local regions of the proteins in assessing their similarity. In essence, the smaller such "deviant" regions, the more similar the two structures are. If one compares two different proteins, where there is not a preassigned correspondence between amino acid residues, a sequence-independent alignment (residue correspondence) has to be generated first, adding another significant level of complexity. The present invention provides a system that takes into account both local and global structure superpositions and is also capable of working without a preassigned residue correspondence.

Evaluating Structure Similarity Between Proteins—Most structure comparison programs are built on the principle that a suitable scoring function can be defined with its optimum corresponding to the most significant structural match for a given protein. Many established comparison techniques evaluate structural similarity by two numbers, the RMSD between two superimposed structures together with the number of "equivalent" (structurally aligned) residues. However, it is very difficult to optimize these two quantities simultaneously, since one can be optimized at the expense of the other. For example, the structural aligner, DALI, which is based on the alignment of distance matrices, solves the optimization problem by combining several numbers into a single quantity, called z-score. ProSup maximizes the number of equivalent residues while RMSD is kept close to a constant value. An additional problem can arise when structures are similar in small, local regions. These regions of similarity can be overlooked when one global superposition is applied. In general, in many cases there is no "best" superposition that reveals all regions of similarity between compared proteins.

To resolve these problems while comparing two structures, the LGA program generates many different local superpositions to detect regions where proteins are similar. The LGA scoring function has two components, LCS (Longest Continuous Segments) and GDT (Global Distance Test), established for the detection of regions of local and global structure similarities between proteins. These two measures were extensively tested during the last three successive rounds of CASP (Critical Assessment of Techniques for Protein Structure Prediction), providing constructive ranking of evaluated 3D models. In comparing two protein structures, the LCS procedure is able to localize and superimpose the longest segments of residues that can fit under a selected RMSD cutoff. The GDT algorithm is designed to complement evaluations made with LCS searching for the largest (not necessary continuous) set of "equivalent" residues that deviate by no more than a specified distance cutoff.

The LCS Algorithm

In an attempt to generate detailed information about regions of local similarity between two protein structures (Molecule1 and Molecule2), or segments thereof, each residue from Molecule2 is assigned to the largest set of residue pairs (C-alpha atoms from Molecule1 and Molecule2) provided it is a part of that set, and can be fit under a selected RMSD (LCS algorithm) or distance (GDT algorithm) cutoff. If an analysis of two structures is based only on the superpositions limited to one selected RMSD or distance cutoff then it would not give full information on similarity between the two structures; some similarities would be detected, some would not. To avoid such limitations, LCS results are generated for a set of increasing RMSD cutoffs (1 Å (Ångstrom), 2 Å, and 5 Å), and in the GDT analysis, two structures are scanned every 0.5 Å, starting from 0.5 Å up to a 10.0 Å distance cutoff. This approach allows us to gather very detailed information on local similarities between two structures. The results of such calculations are reported in the format as shown in Table 1 which provides an Example of data generated by LCS and GDT analyses.

TABLE 1

| | | | | | | | | | | | | | | | | |
|---|---|---|---|---|---|---|---|---|---|---|---|---|---|---|---|---|
| | | | | | | | | Column # | | | | | | | | |
| 2 | 3 | 4 | 5 | 6 | 7 | 8 | 9 | 10 | 11 | 12 | 13 | 14 | 15 | 16 | 17... | |
| | | | | | | | | | | Cutoffs: | | | | | | |
| | | | | 1Å | 2Å | 5Å | 0.5Å | 1.0Å | 1.5Å | 2.0Å | 2.5Å | 3.0Å | 3.5Å | 4.0Å | 4.5Å... | |
| LCS_GDT | MOLECULE-1 | | MOLECULE-2 | | LENGTH_OF_THE | | | | | | | | | | | |
| LCS_GDT | RESIDUE | | RESIDUE | | CONTINUOUS | | | | | | | | | | | |
| LCS_GDT | NAME | NUMBER | NAME | NUMBER | | SEGMENT | | | | GLOBAL DISTANCE TEST DATA | | | | | | |
| LCS_GDT | V | 40 | A | 29 | 23 | 26 | 90 | 10 | 18 | 22 | 23 | 24 | 24 | 27 | 33 | 49... |
| LCS_GDT | A | 41 | Q | 30 | 23 | 26 | 90 | 10 | 18 | 22 | 23 | 24 | 25 | 27 | 42 | 55... |
| LCS_GDT | L | 42 | L | 31 | 23 | 26 | 90 | 4 | 7 | 20 | 23 | 24 | 25 | 36 | 46 | 55... |
| LCS_GDT | E | 43 | E | 32 | 8 | 26 | 90 | 4 | 7 | 15 | 23 | 24 | 25 | 35 | 46 | 55... |
| LCS_GDT | Q | 44 | V | 33 | 8 | 26 | 90 | 4 | 6 | 9 | 18 | 24 | 26 | 37 | 46 | 55... |
| LCS_GDT | T | 45 | T | 34 | 8 | 26 | 90 | 4 | 7 | 9 | 13 | 22 | 25 | 36 | 46 | 55... |
| LCS_GDT | G | 46 | G | 35 | 8 | 14 | 90 | 3 | 7 | 9 | 12 | 17 | 22 | 35 | 46 | 55... |

In the output shown in Table 1, columns 2-5 provide information on residues from two compared structures, and columns 6, 7, and 8 show the results from LCS analyses under 1 Å, 2 Å, and 5 Å RMSD cutoffs, respectively. For example, residue L-31 from Molecule 2 is a member of a 23-residue long continuous segment that can be superimposed with corresponding residues from Molecule 1 under a 1 Å RMSD cutoff, but residue E-32 is an element of a segment consisting of just 8 residues at an RMSD cutoff of 1 Å. In columns 9-28 the results of GDT analysis under 0.5 Å through 10.0 Å distance cutoffs are reported. For example, residue E-32 belongs to a set of 4 residues (not necessarily continuous) that can fit under a 0.5 Å distance cutoff, a set of 7 residues under a 1.0 Å, and a 25-residue set under 3.0 Å.

The GDT Algorithm

In the GDT procedure, the search for an optimal superposition between two structures is performed as follows. For each selected pair of 3, 5 and 7 residue-long segments from both structures, an RMSD and a superposition are calculated. Each calculated superposition is used as a starting point to give an initial list of equivalent residues (C-alpha atom pairs from Molecule 1 and Molecule 2). The list of such equivalences is iteratively extended to collect the largest set of residues that can fit under a given distance cutoff. The goal of the designed and implemented iterative procedure is to exclude atoms that are more distant than a threshold (distance cutoff) between Molecule 1 and Molecule 2 after the transform is applied. Starting from the initial set of atom pairs, the algorithm is as follows: a) obtain the transform, b) apply the transform, c) identify all atom pairs for which the distance is larger than the threshold, d) re-obtain the transform, excluding those atoms, e) repeat steps b)-d) until the set of atoms used in calculations is the same for two cycles running.

The LCS and GDT Algorithms are Complementary—Results of the LCS algorithm identify local regions of similarity between proteins, while residues identified by GDT arise from anywhere in the structure (i.e., sequence continuity need not be maintained). From this point of view, GDT detects global, as opposed to local, similarity. Using GDT Applicant focused on distance rather than RMSD. Using LCS, however, we can optimize (minimize) RMSD on the selected residues. So from this point of view, LCS gives complete and optimal information. Working with distance analysis (maximum norm) an optimal method for finding the "best superposition," which will minimize the distances between all selected residues, is not known. Results can only be approximated. So to find the "best" global structural match, GDT uses many distance cutoffs and superpositions. The GDT algorithm "tests" each residue one by one from Molecule2, trying to assign it to the largest set of residues possible (not necessarily continuous) deviating from Molecule1 by no more than a specified distance cutoff. GDT evaluates a selected but large number of superpositions, in effect yielding consistently reliable results.

Description of the LGA_S Scoring Function

By combining these two techniques (LCS-RMSD based and GDT-distance based), LGA not only calculates a "best" superposition between two proteins (meaning "under certain RMSD and distance cutoffs"), but also identifies the regions of local similarity between compared structures. In the structure alignment search procedure, for each generated list of equivalent residues, the following values are calculated: LCS_vi—percent of residues (continuous set) that can fit under an RMSD cutoff of vi Å (for vi=1.0, 2.0, . . . ), and GDT_vi—an estimation of the percent of residues (largest set) that can fit under the distance cutoff of vi Å (for vi=0.5, 1.0, . . . ). A scoring function (LGA_S) can be defined as a combination of these values and can be used to evaluate the level of structure similarity of selected regions. For a given parameter w (0.0<=w<=1.0), representing a weighting factor, we calculate LGA_S by the formula: LGA_S=w*S(GDT)+ (1−w)*S(LCS) where S(F) function is defined as follows:

```
For each vi (v1, v2, . . . , vk) {
    Y = (k−i+1)/k; X = X + Y*F_vi;
}
S(F) = X/((1+k)*k/2);
```

The same scoring function is applied by the LGA program to perform the selection and ranking of the regions of structure similarities in the sequence dependent mode of analysis as well as in the sequence independent mode.

Graphical Presentation of the Results from LGA

How can the results of a multiple superposition (see Table 1.) between two structures be visualized? Let us compare an NMR average model, 1m2e_A, of the N-terminal domain of Synechococcus Elongatus Kaia (KAIA135N) with its 25-member family of low energy (designated 1m2f_A_n). In Table 2, NMR models are sorted by GDT_TS values.

TABLE 2

| Model | N1 | N2 | DIST | N | RMSD | GDT_TS |
|---|---|---|---|---|---|---|
| 1m2f_A_8 | 135 | 135 | 3.0 | 135 | 0.79 | 97.037 |
| 1m2f_A_16 | 135 | 135 | 3.0 | 133 | 0.70 | 96.296 |
| 1m2f_A_17 | 135 | 135 | 3.0 | 133 | 0.80 | 96.296 |
| 1m2f_A_2 | 135 | 135 | 3.0 | 135 | 0.91 | 96.296 |
| 1m2f_A_1 | 135 | 135 | 3.0 | 133 | 0.93 | 96.111 |
| 1m2f_A_19 | 135 | 135 | 3.0 | 134 | 0.95 | 96.111 |
| 1m2f_A_11 | 135 | 135 | 3.0 | 134 | 0.84 | 95.926 |
| 1m2f_A_14 | 135 | 135 | 3.0 | 133 | 0.91 | 95.926 |
| 1m2f_A_20 | 135 | 135 | 3.0 | 133 | 0.94 | 95.926 |
| 1m2f_A_7 | 135 | 135 | 3.0 | 131 | 0.85 | 95.741 |

TABLE 2-continued

| Model | N1 | N2 | DIST | N | RMSD | GDT_TS |
|---|---|---|---|---|---|---|
| 1m2f_A_21 | 135 | 135 | 3.0 | 130 | 0.80 | 95.556 |
| 1m2f_A_5 | 135 | 135 | 3.0 | 134 | 1.04 | 95.556 |
| 1m2f_A_10 | 135 | 135 | 3.0 | 135 | 1.09 | 95.556 |
| 1m2f_A_18 | 135 | 135 | 3.0 | 134 | 0.89 | 95.370 |
| 1m2f_A_12 | 135 | 135 | 3.0 | 133 | 0.92 | 95.370 |
| 1m2f_A_13 | 135 | 135 | 3.0 | 131 | 0.95 | 95.370 |
| 1m2f_A_15 | 135 | 135 | 3.0 | 130 | 0.80 | 95.185 |
| 1m2f_A_24 | 135 | 135 | 3.0 | 133 | 0.89 | 95.185 |
| 1m2f_A_22 | 135 | 135 | 3.0 | 131 | 0.85 | 95.000 |
| 1m2f_A_25 | 135 | 135 | 3.0 | 134 | 0.94 | 95.000 |
| 1m2f_A_9 | 135 | 135 | 3.0 | 132 | 1.14 | 95.000 |
| 1m2f_A_4 | 135 | 135 | 3.0 | 130 | 1.01 | 94.444 |
| 1m2f_A_3 | 135 | 135 | 3.0 | 129 | 0.74 | 94.074 |
| 1m2f_A_23 | 135 | 135 | 3.0 | 132 | 1.00 | 93.704 |
| 1m2f_A_6 | 135 | 135 | 3.0 | 130 | 1.05 | 92.963 |

In Table 2 the NMR models 1m2f_A_1-1m2f_A_25 compared to an average model 1m2e_A and sorted by GDT_TS value where GDT_TS=(P1+P2+P4+P8)/4, and Pd is a percent of residues from 1m2e_A that can be superimposed with corresponding residues from 1m2f_A_n under selected distance cutoffs d=1, 2, 4, 8.

Figure 2:
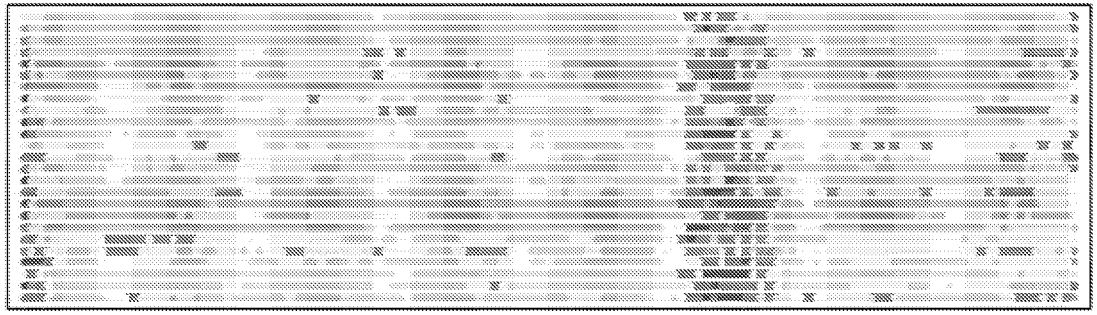
FIG. 2 shows a strip chart used to plot output from the standard structure comparison analysis of protein structures.
Figure 3:
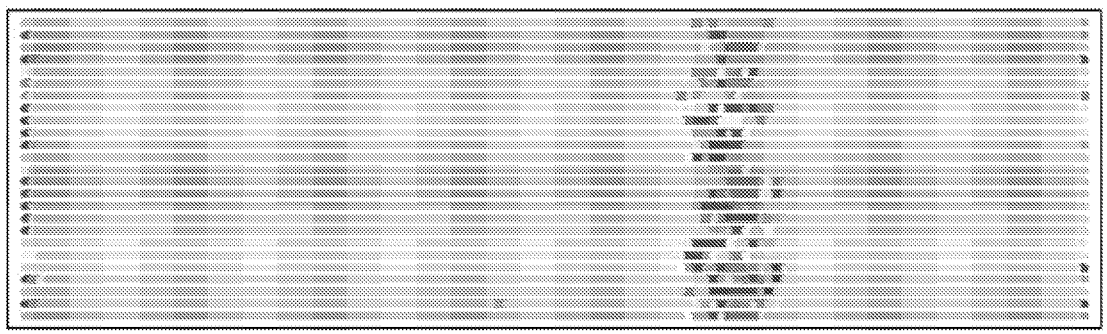
FIG. 3 shows the strip chart representing the results from the LGA analysis (the regions of the structure deviation are clearly detected).
Figure 4:
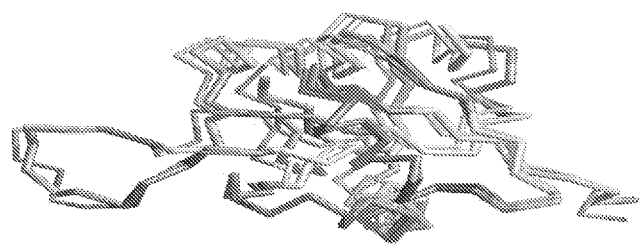
FIG. 4 illustrates 3D plot (backbone representation) of the structure superposition of two structures. Plot corresponds to the fourth strip bar from the FIG. 2.
Figure 5:
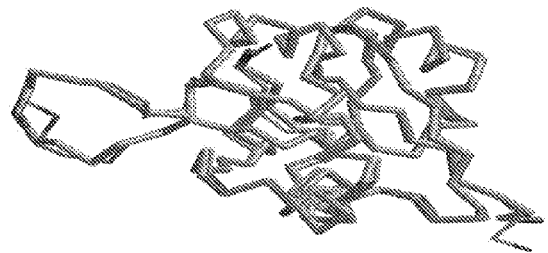
FIG. 5 illustrates 3D plot (backbone representation) of the structure superposition of two structures. Plot corresponds to the fourth strip bar from the FIG. 3. representing the results from the LGA analysis.

Referring now to FIGS. 2 and 3, it is shown how strip charts can be used to plot output from the LGA program (data from Tables 1 and 2) of the system 100. Each bar from FIGS. 2 and 3 corresponds to one pair of analyzed structures. The ordering of bars is the same as in Table 2. Rasmol plots. FIGS. 4 and 5 are provided only for one model, 1m2f_A_2 (fourth in Table 2 and bar charts).

In FIG. 2, C-alpha-C-alpha distance deviation bars from one LGA superposition under a 3.0 Å distance cutoff. Residues superimposed below 1.0 Å are gray, below 2.0 Å in light-gray, below 3.0 Å in dark-gray, below 4.0 Å in very dark-gray, and residues at or above 4.0 Å in black. c) Rasmol plot of two superimposed structures: 1m2f_A_2 and 1m2e_A. Colors correspond to the fourth bar from a). b) C-alpha-C-alpha deviation bars for multiple LGA superpositions. d) Rasmol plot of superimposed structures 1m2f_A_2 and 1m2e_A corresponding to fourth bar representation from c) where more than 85.0 percent of equivalent residues under distance cutoff=1.5 Å are in gray, more than 70.0 percent: light-gray, more than 50.0 percent: dark-gray, and less than or equal to 20.0 percent: black.

FIG. 3 shows that the results of multi-superposition LGA analysis as reported in Table 1 can be used to detect regions of similarity between proteins from those where the structures differ. Analysis based on a single superposition does not distinguish the regions of similarity so clearly.

Graphical Presentation of Results from Sequence Independent Database Searches—The greatest utility of structure alignment programs, such as LGA, lies in their ability to superimpose protein structures regardless of sequence identity and to detect regions of structural similarity. In Table 3 a list of ten of the closest PDB structural matches to the already mentioned NMR average model 1m2e_A (CASP5 target T0138) is provided. The PDB database search was performed with the use of the LGA program working in sequence independent mode. The level of sequence identity (Seq_Id) to other structurally similar PDB entries was very low, on the order of 12%.

TABLE 3

| Name | N1 | N2 | DIST | N | RMSD | Seq_Id | LGA_S |
|---|---|---|---|---|---|---|---|
| 1a04_B | 205 | 135 | 5.0 | 118 | 2.36 | 11.86 | 63.707 |
| 1a2o_B | 347 | 135 | 5.0 | 117 | 2.47 | 11.97 | 62.598 |
| 1rml | 200 | 135 | 5.0 | 116 | 2.14 | 12.07 | 69.416 |
| 1e6m_A | 128 | 135 | 5.0 | 116 | 2.23 | 10.34 | 64.587 |
| 6chy_A | 128 | 135 | 5.0 | 116 | 2.25 | 10.34 | 63.363 |
| 6chy_B | 128 | 135 | 5.0 | 116 | 2.26 | 10.34 | 64.196 |
| 2che | 128 | 135 | 5.0 | 116 | 2.28 | 9.48 | 64.372 |
| 1a0o_C | 128 | 135 | 5.0 | 116 | 2.29 | 10.34 | 63.826 |
| 1ffg_C | 128 | 135 | 5.0 | 116 | 2.29 | 10.34 | 63.161 |
| 1ffw_A | 128 | 135 | 5.0 | 116 | 2.32 | 9.48 | 62.522 |

Table 3 is a list of the ten of the closest PDB structures to 1m2e_A found by the LGA program. Proteins are sorted by N—the number of superimposed residues under a distance cutoff 5.0 Å.

Figure 6:
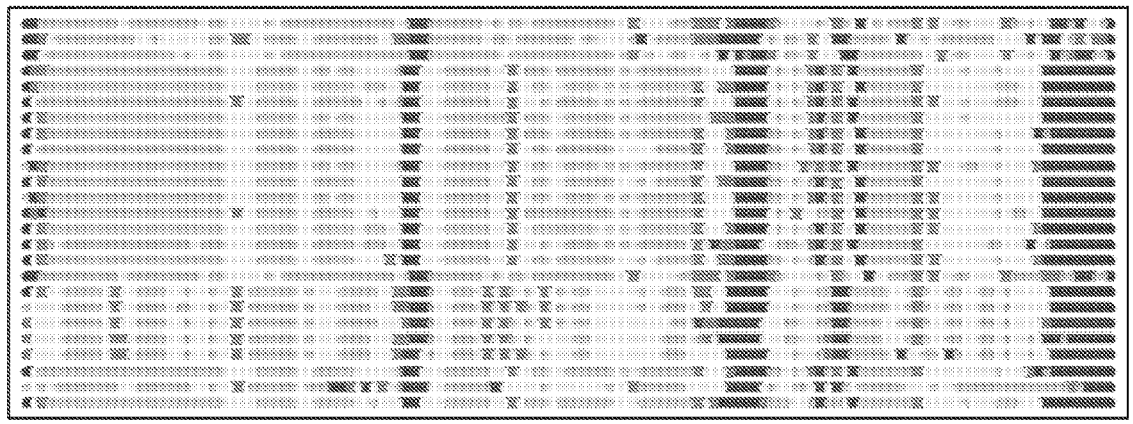
FIG. 6 is a bar representation of the results from sequence independent LGA superpositions.

A graphical presentation of the results from the LGA database search is given in FIG. 6. Each bar corresponds to one hit to a protein from the PDB database. The bars are ordered as in Table 3. FIG. 6 is a bar representation of the results from sequence independent LGA superpositions, and a FIG. 7 (backbone representation, rasmol plot) of superimposed first template 1a04_B and T0138. Residues superimposed below 2.0 Å are in gray, below 4.0 Å in light-gray, below 6.0 Å in dark-gray, and residues at or above 6.0 Å or not superimposed are in black (target) and in white (template).

Figure 7:
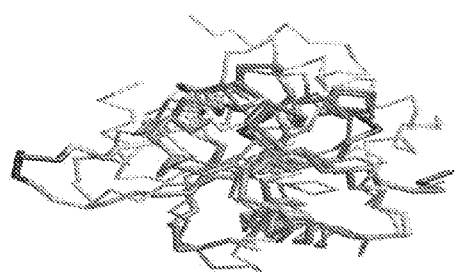
FIG. 7 shows regions of structural similarity in 3D plot (backbone representation) between the reference structure.

FIG. 7 shows regions of structural similarity between the reference structure T0138 (in PDB 1m2e_A), and the best database match, PDB protein, 1a04_B (see Table 3, and first bar from FIG. 6). Regions of high structural diversity are shown in black and dark-gray.

The number N of structurally equivalent residues differs considerably for several protein pairs. It might be expected that a higher number of equivalent residues would indicate better performance of a particular method in the detection of structural similarity. However, comparing the number of equivalent residues is insufficient without taking RMSD into account. RMSD reported by LGA is fairly constant in all cases. Applicant's program can keep the smallest range of RMSD 1.9-2.6 while providing a high number of aligned residues. In a comparison to ProSup, in some cases LGA superimposes more residues under the same distance cutoff (sometimes with a slightly higher value of RMSD). During the CASP4 competition, both programs were used for evaluation of structure predictions and to perform PDB searches showing similar results.

Applicant's approach of "Optimizing the number of equivalent residues while keeping the RMSD and DISTANCE deviations constant" provides a simple and intuitive measure of structure similarity. Such a measure can be used effectively for ranking in database searches. Applicants show that in LGA an additional requirement of fulfilling distance restrictions combined with extensive analysis of regions of local similarities (from searches with multiple distance and RMSD cutoffs) was successfully implemented. Applicant's approach can generate data that provide detailed information not only about the degree of global similarity but also about regions of local similarity in protein structures. It allows the clustering of similar fragments of structures, and the use of such clusters to identify sequence patterns that would represent local structural motifs.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A computer-implemented method of generating a local-global alignment score that indicates a global and a local similarity between a first protein structure and a second protein structure, the method executed by a computer system and comprising:
receiving, at the computer system, a protein structure correspondence having a plurality of positions indicating a corresponding pair of residues in the first protein structure and the second protein structure;
determining, by the computer system and according to a plurality of specified threshold values, a plurality of root mean square deviations corresponding to a plurality of sets of pairs of residues, each set including a plurality of pairs of residues that are contiguous in the protein structure correspondences;
selecting, by the computer system, a longest contiguous segment corresponding to a set of pairs of residues of the plurality of pairs of residues based on the plurality of root mean square deviations;
determining, by the computer system, a global distance test value based on a plurality of distance scores, each score corresponding to a number of pairs of residues in the correspondence within a pre-defined distance of a plurality of pre-defined distances;
generating, by the computer system, the local-global alignment score based on the longest contiguous segment and the global distance test value; and
providing, by the computer system, a result based on the local-global alignment score.

2. The method of claim 1, wherein the computer system includes a server and the method further comprises:
receiving, at the server, a first set of co-ordinates associated with the first protein structure from a client;
receiving, at the server, a second set of co-ordinates associated with the second protein structure; and
the server generating the protein structure correspondence based on the first set of co-ordinates and the second set of co-ordinates.

3. The method of claim 1, further comprising:
receiving, at the computer system, a first set of co-ordinates associated with the first protein structure;
receiving, at the computer system, a second set of co-ordinates associated with the second protein structure; and
generating, by the computer system, the protein structure correspondence based on the first set of co-ordinates and the second set of co-ordinates.

4. The method of claim 3, wherein providing a result based on the local-global alignment score further comprises:
generating, by the computer system, a second protein structure correspondence based on the local-global alignment score; and
providing, by the computer system, the second protein structure correspondence.

5. The method of claim 3, wherein providing the second protein structure correspondence comprises:
the computer system modifying the set of co-ordinates specifying the first protein structure based on at last one of the global distance test value and the longest continuous segment to generate a second set of co-ordinates specifying the first protein structure; and the computer system providing the second set of co-ordinates.

6. The method of claim 4, wherein providing the second protein structure correspondence comprises:
the computer system displaying a graphical representation of at least one of the first protein structure or the second protein structure, wherein at least some of the residues in the graphical representation are colored according to distance between the at last some of the residues and the corresponding residues in the second protein structure.

7. The method of claim 6, wherein the graphical representation is a bar plot.

8. The method of claim 6, wherein the graphical representation is a three-dimensional protein structure.

* * * * *